US00PP29287P3

(12) United States Plant Patent
Brazelton et al.

(10) Patent No.: US PP29,287 P3
(45) Date of Patent: May 15, 2018

(54) BLUEBERRY PLANT NAMED 'FCM12-087'

(50) Latin Name: ***Vaccinium corymbosum* hybrid**
Varietal Denomination: FCM12-087

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Eugene, OR (US); Antonio A. Alamo Bermudo, Seville (ES)

(73) Assignee: Fall Creek Farm & Nursery, Lowell, OR (US)

( * ) Notice: Subject to any disclaimer, the term of this patent is extended or adjusted under 35 U.S.C. 154(b) by 0 days. days.

(21) Appl. No.: 15/330,397

(22) Filed: Sep. 15, 2016

(65) Prior Publication Data

US 2017/0099755 P1 Apr. 6, 2017

Related U.S. Application Data

(60) Provisional application No. 62/284,549, filed on Oct. 2, 2015.

(51) Int. Cl.
*A01H 5/08* (2006.01)

(52) U.S. Cl.
USPC ..... Plt./157

(58) Field of Classification Search
USPC ..... Plt./156, 157
See application file for complete search history.

*Primary Examiner* — Susan McCormick Ewoldt
(74) *Attorney, Agent, or Firm* — Hahn Loeser & Parks, LLP

(57) ABSTRACT

The new blueberry plant variety 'FCM12-087' is provided. 'FCM12-087' is a commercial variety intended for the hand harvest fresh market. The new blueberry plant originated from a cross of 'FL00-180' (female parent, unpatented) by 'FF-124' (pollen parent, unpatented), which can be distinguished by its outstanding features. The new blueberry plant 'FCM12-087' as it grows in Tala, Mexico is distinguished by a spreading growth habit, with slightly weeping laterals, very narrowly spaced internodes, and highly evergreen leaves. The new blueberry plant 'FCM12-087' has new leaves that are bluish-green in hue and rounded in shape. The flowers of 'FCM12-087' are urceolate in shape, and the fruit is firm, large, light blue in color and possesses a flattened shape.

6 Drawing Sheets

Latin name of the genus, and species:
Genus—*Vaccinium.*
Species—*corymbosum* hybrid.
Variety denomination: The new blueberry plant claimed is of the variety denominated 'FCM12-087'.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry (*Vaccinium corymbosum* L. hybrid) plant, referred to as 'FCM12-087', as herein described and illustrated. The new blueberry plant variety 'FCM12-087' was selected near Colima, state of Colima, Mexico in 2012. 'FCM12-087' is a commercial variety intended for the hand harvest fresh market. The variety has high vigor and ripens the majority of its fruit later than the variety 'Biloxi' (not patented). The berry of 'FCM12-087' has good firmness, strong bloom and light blue color, and a small picking scar on fruit derived from the current season's growth. 'FCM12-087' was selected for use in an evergreen production system in areas where zero effective chilling hours may be accumulated. The growing region of Colima, Mexico where 'FCM12-087' was originally selected is at a low latitude (~19.5° N) with a sub-tropical climate. In this region, temperatures rarely fall below 45° F. (the maximum temperature at which blueberry buds accumulate chill units to break dormancy) and day lengths only vary from between 10.8 hours in December to 13.2 hours in June. Under these conditions, many traditional low-chill blueberry varieties (developed in latitudes 25°-35°) do not produce flower buds or flowers. In the case of blueberry varieties that do flower under these conditions, the flowers are produced primarily on the current season's growth that is often referred to as a 'primocane' in the blueberry industry. The 'primocane' inflorescences tend to be very elongated in form compared to the inflorescence produced at higher latitudes from dormant buds, and the fruit often does not abscise well from the pedicel, resulting in a large picking scar which greatly limits shelf life. The blueberry industry in this area is dominated by the variety 'Biloxi' (not patented). 'Biloxi' (not patented) is one of the few traditional low chill varieties that grows well and produces fruit with a good picking scar in this growing environment. However, 'Biloxi' (not patented) often produces an excessive proportion of small, unmarketable fruit. 'FCM12-087' was exceptional because it flowered and fruited more than most genotypes but also had larger fruit than Biloxi (not patented) with a small picking scar. 'FCM12-087' also flowers later after pruning than 'Biloxi' (not patented) and produces significant numbers of flower buds in a zero chill climate, resulting in a harvest window that is later and more concentrated than 'Biloxi' (not patented) (which fruits more heavily on primocanes).

SUMMARY OF THE INVENTION

Pedigree and History: The new blueberry plant originated from a cross of 'FL00-180' (female parent, unpatented) by 'FF-124' (pollen parent, unpatented).

The cross that produced 'FCM12-087' (denominated by the cross code 'X08-165') was made in Lowell, Oreg., USA in 2008.

The new blueberry plant variety 'FCM12-087' was initially propagated by softwood cuttings in 2012 in Lowell, Oreg., USA. Rooted plants from these cuttings were field planted in Tala, Jalisco, Mexico and also shipped to Lowell, Oreg., USA in 2013. Additional plants have been propagated via softwood cuttings from the plants established in Tala, Mexico in 2014. The plants sent to Lowell, Oreg. were also propagated via softwood cuttings in 2014 and successfully used to establish in vitro culture lines in 2014.

The seedling family that produced 'FCM12-087' was initially grown in 50 cell propagation trays and shipped to Mexico in March, 2011 after the plants had reached sufficient size to be field planted. They were planted in a commercial blueberry field near Colima City, state of Colima, Mexico and evaluated for fruit production and quality beginning in December 2011. 'FCM12-087' was selected in 2012 because it had large, light blue fruit and good fruit yield in an evergreen, zero chill production system. After being selected in Colima, 'FCM12-087' was propagated by softwood cuttings and a ten plant plot was established in Tala, Mexico (near Guadalajara). The ten plant plot was evaluated for fruit quality and yield in comparison to the standard varieties 'Biloxi' (not patented) and 'Ventura' (U.S. Plant Pat. No. 24,606) beginning in December, 2013. During evaluation in the ten plant plot, it was also observed that 'FCM12-087' had very high yield and ripened the majority of its fruit after 'Biloxi'. It was also observed that 'FCM12-087' had good heat tolerance during fruit ripening and it produced fruit that stored exceptionally well. After two harvest seasons of evaluation, the yield and fruit quality of 'FCM12-087' were deemed sufficiently good to warrant launching it as a commercial variety.

The new blueberry plant 'FCM12-087' as it grows in Tala, Mexico is distinguished by a spreading growth habit, with slightly weeping laterals, very narrowly spaced internodes, and highly evergreen leaves. The new blueberry plant 'FCM12-087' has new leaves that are bluish-green in hue and rounded in shape. The flowers of 'FCM12-087' are urceolate in shape, and the fruit is firm, large, light blue in color and possesses a flattened shape. The new blueberry plant 'FCM12-087' consistently produces larger fruit than the standard variety 'Biloxi' (not patented), which is a very desirable characteristic.

Plants of 'FCM12-087' propagated from softwood cuttings or in vitro are phenotypically stable and exhibit the same characteristics as the original plant. The parents 'FL00-180' (not patented) and 'FF-124' (pollen parent, unpatented) have not been evaluated in the same environment of Mexico that 'FCM12-087' was selected in. In California, USA 'FL00-180' (not patented) has very evergreen leaves and fruit of 'FL00-180' (not patented) were firm, light blue in color, with an exceptionally small picking scar and thick skin. In comparison to 'FL00-180' (not patented), 'FCM12-087' fruit has a larger picking scar. The parent 'FF-124' was also not observed in Mexico where 'FCM12-087' was selected. In California, USA and Huelva, Spain, 'FF-124' (pollen parent, unpatented) was very early ripening and produced light blue fruit that was soft. In comparison to 'FF-124' (pollen parent, unpatented), fruit of 'FCM12-087' are more firm.

DETAILED BOTANICAL DESCRIPTION

Figure 1:
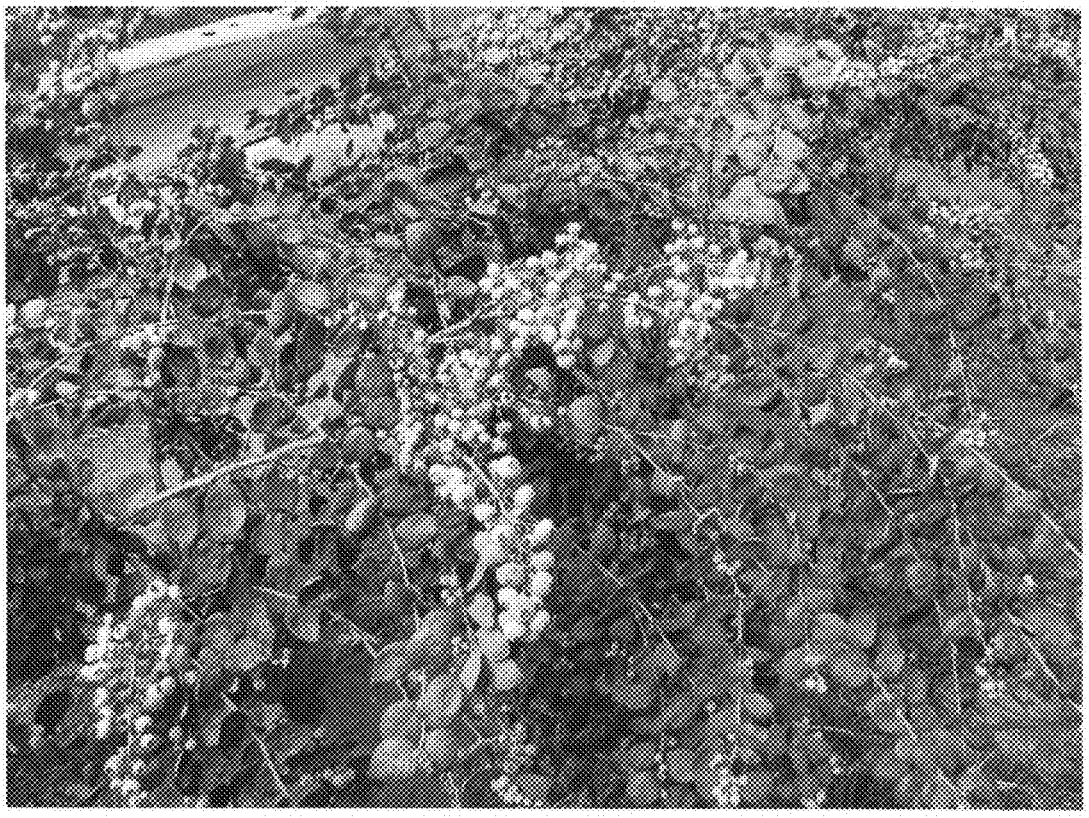
FIG. 1 is a photograph of 'FCM12-087' grown in Tala, Mexico and photographed on Feb. 24, 2015.
Figure 2:
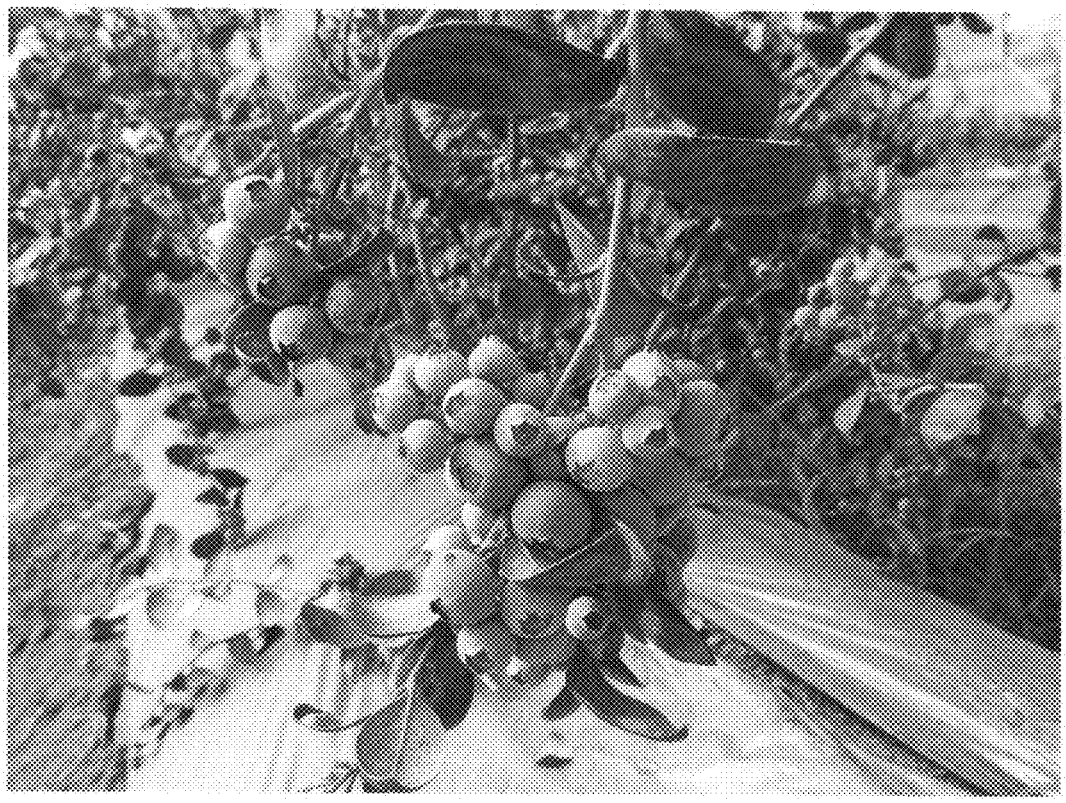
FIG. 2 is a photograph of fruit clusters of 'FCM12-087' on the plant, grown in Tala, Mexico and photographed on Feb. 25, 2015.
Figure 3:
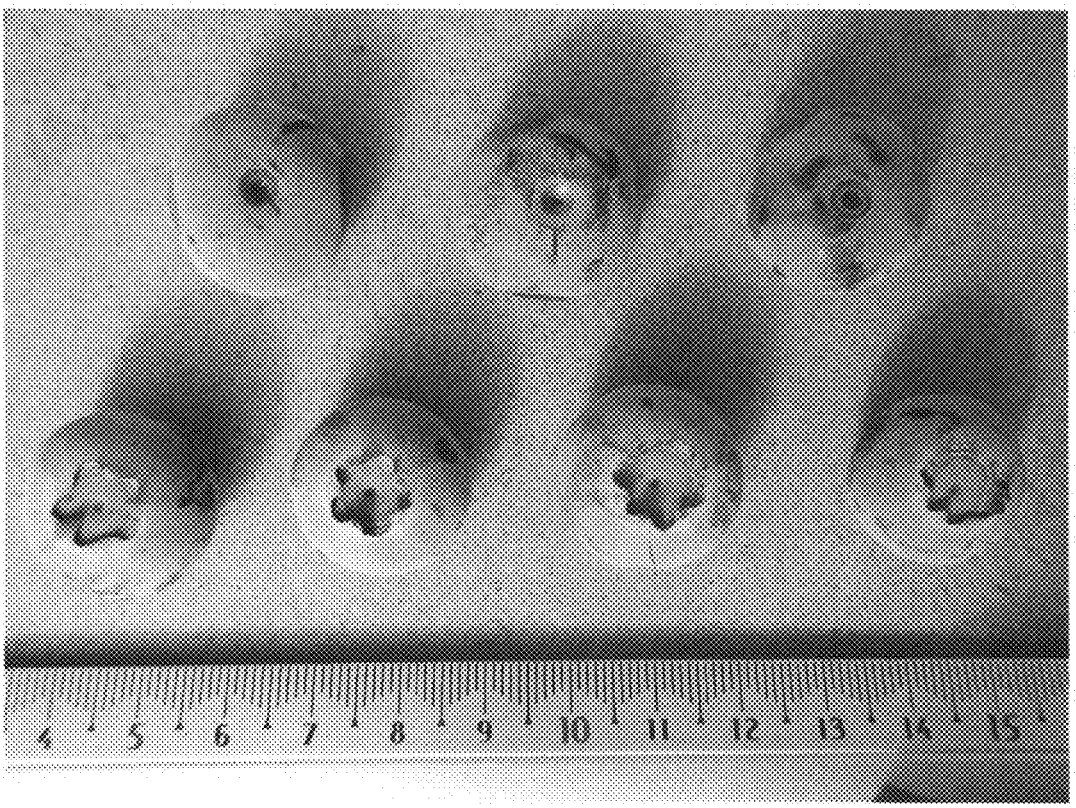
FIG. 3 is a photograph of fruit of 'FCM12-087', grown in Tala, Mexico and photographed on Feb. 26, 2015.
Figure 4:
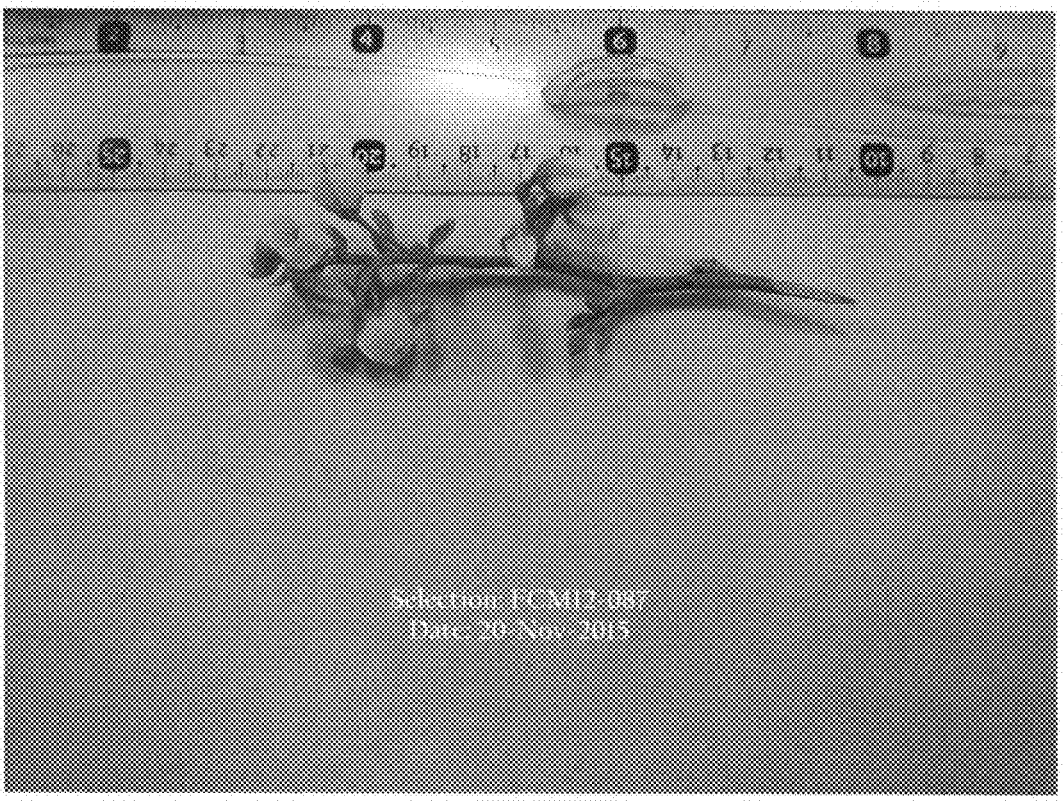
FIG. 4 is a photograph of flowers of 'FCM12-087', grown in Tala, Mexico and photographed on Nov. 20, 2015.
Figure 5:
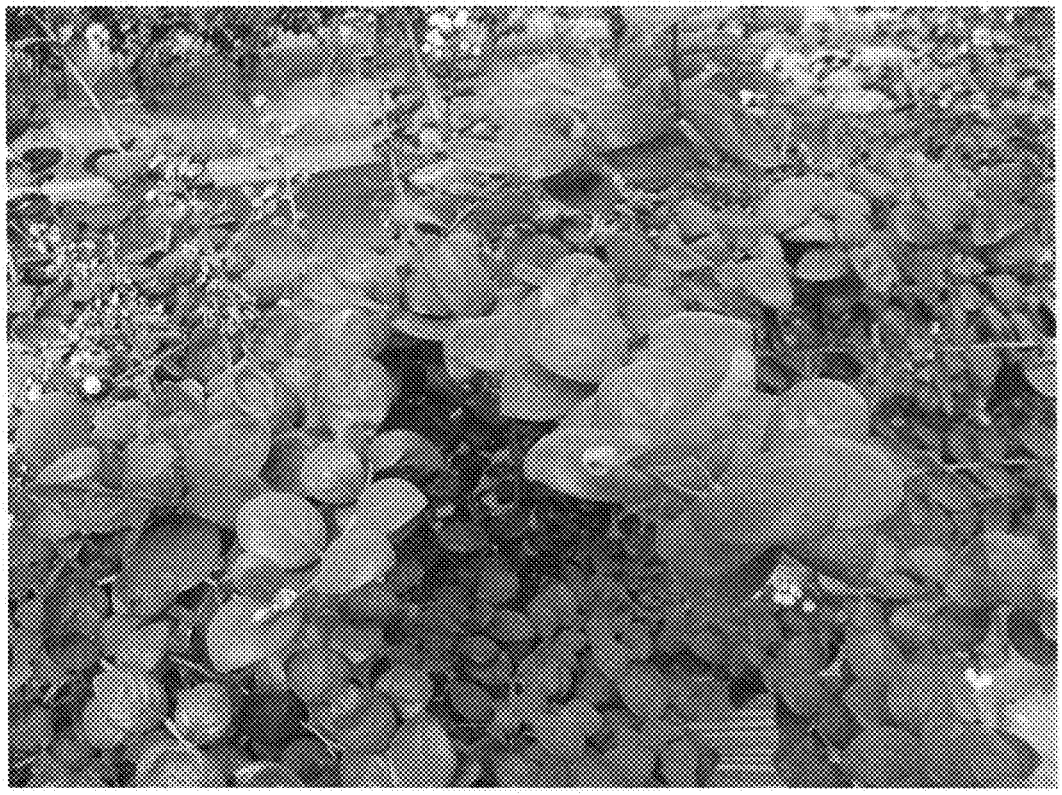
FIG. 5 is a photograph of leaves and new shoots of 'FCM12-087' growing in Mexico showing the waxy surface and slightly blue color of new leaves. Photographed on Nov. 24, 2014.
Figure 6:
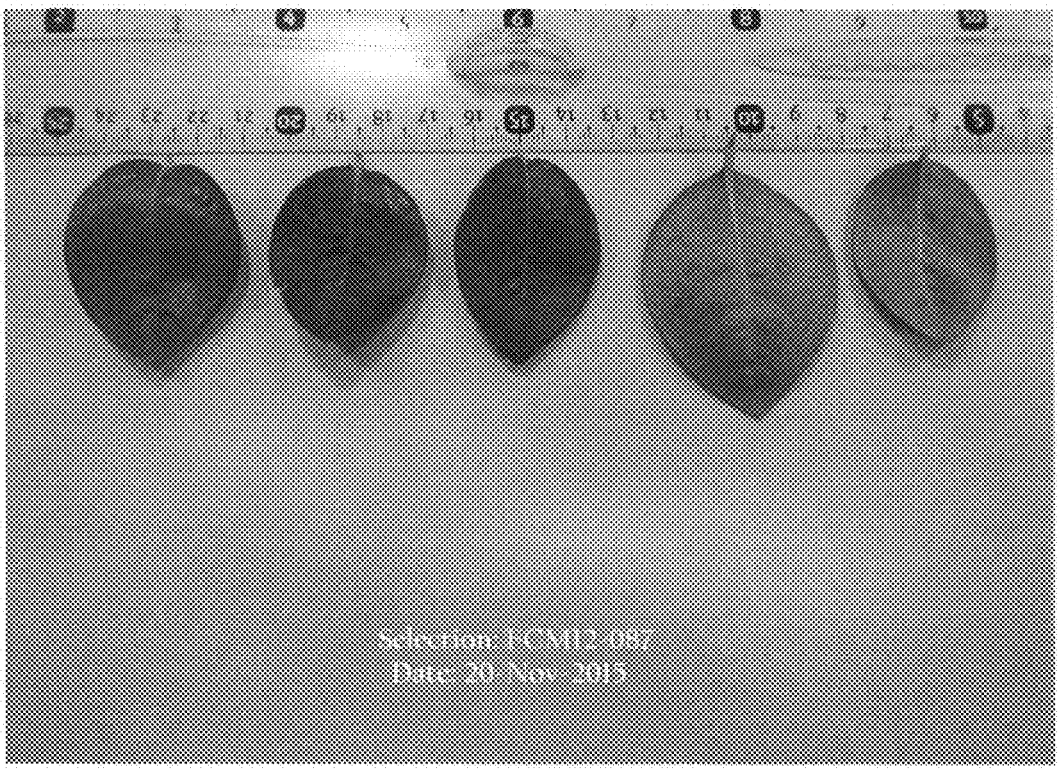
FIG. 6 is a photograph of leaves of 'FCM12-087' grown in Tala, Mexico showing upper and lower leaf surface. Photographed on Nov. 20, 2015.

The following detailed description sets forth the distinctive characteristics of 'FCM12-087'. The data which defines these characteristics was collected from asexual reproductions of the original selection. Dimensions, sizes, colors, and other characteristics are approximations and averages set forth as accurately as possible. All measurements are the average of five observations. The plant history was taken on mature plants approximately 2 years of age, and the descriptions relate to plants grown in the field in Tala, state of Jalisco, Mexico unless otherwise noted (observations on fall leaf color and some other traits were collected on plants grown in Lowell, Oreg.). Descriptions of fruit characteristics were made on fruit grown in Tala, State of Jalisco, Mexico. Color designations are from "The Pantone Book of Color" (by Leatrice Eiseman and Lawrence Herbery, Harry N. Abrams, Inc., Publishers, New York 1990) unless noted otherwise. Where the Pantone color designations differ from the colors in the photographs, the Pantone colors are accurate.

VARIETY

Classification:

*a. Family.*—Ericaceae.

*b. Genus.*—*Vaccinium.*

*c. Species.*—*corymbosum* hybrid.

*d. Common Name.*—Southern Highbush Blueberry.

Parentage:

*a. Female parent.*—'FL00-180' (not patented).

*b. Male parent.*—'FF-124' (pollen parent, unpatented).

Market class: Commercial blueberry variety intended for the hand harvest fresh market.

PLANT

General:

a. *Parentage*.—Female parent 'FL00-180' (unpatented) Male parent 'FF-124' (pollen parent, unpatented).
b. *Plant height*.—Average 115 cm.
c. *Plant width*.—108.6 cm.
d. *Growth habit*.—Semi-prostrate.
e. *Growth*.—Moderate vigor.
f. *Productivity*.—Excellent, average of 3.63 kilos per plant, per season on a 2 year old plant, compared to 1.86 kilos per plant per season for the commercial variety 'Biloxi' (not patented).
g. *Cold hardiness*.—Not determined, likely USDA zone 7 given southern highbush parentage.
h. *Chilling requirement*.—Not determined, estimated at less than 700 hours less than 45 degrees Fahrenheit. Capable of fruiting well with zero chill hours when maintained in an evergreen state of growth.
i. *Leafing*.—Excellent leafing.
j. *Twigginess*.—Moderately twiggy.

STEM

General:

a. *Suckering tendency*.—High.
b. *Mature cane color*.—Pantone Spinach Green 16-0439.
c. *Mature cane length*.—Average of 55 cm.
d. *Mature cane width*.—Average of 15.35 mm on a two year old plant.
e. *Bark texture*.—Rough.
f. *Fall color on new shoots*.—Not evaluated.
g. *Surface texture of new wood*.—Smooth.
h. *Internode length on strong, new shoots*.—Average of 16.164 mm.
i. *Average number of buds per fruiting lateral*.—Average of 5.8.

FOLIAGE

General:

a. *Leaf bases*.—Obtuse.
b. *Leaf length*.—Average of 55.6 mm.
c. *Leaf width*.—Average of 33.0 mm.
d. *Leaf length/width ratio*.—1.68, moderately wide.
e. *Leaf nectaries*.—Absent.
f. *Pubescence of upper side*.—Absent.
g. *Pubescence of lower side*.—Absent.
h. *Cross sectional profile*.—Revolute.
i. *Longitudinal profile*.—Slightly undulate.
j. *Attitude*.—Porrect.
k. *Leaf width*.—Average of 33.0 mm.
l. *Leaf length/width ratio*.—1.68, moderately wide.
m. *Leaf nectaries*.—Absent.
n. *Pubescence of upper side*.—Absent.
o. *Pubescence of lower side*.—Absent.
p. *Cross sectional profile*.—Revolute.
q. *Longitudinal profile*.—Slightly undulate.
r. *Attitude*.—Porrect.
s. *Time of beginning of leaf bud burst*.—Not determined.
t. *Leaf color* (*top side*).—Pantone Chive 19-0323.
u. *Leaf color* (*under side*).—Pantone Mistletoe 16-0220.
v. *Leaf arrangement*.—Alternate.
w. *Leaf shape*.—Broadly elliptic to ovate.
x. *Leaf margins*.—Entire.
y. *Leaf venation*.—Pinnate/anastomosing.
z. *Leaf apices*.—Acute.

Petioles:

a. *Length*.—Average of 3.57 mm.
b. *Width*.—Average of 2.17 mm.
c. *Color*.—Pantone Tarragon 15-0326.
d. *Surface texture*.—Smooth.

FLOWERS

General:

a. *Time of beginning of flowering*.—In Tala, Mexico approximately September 15 depending on timing of previous pruning.
b. *Time of* 50% *anthesis*.—In Tala, Mexico approximately October 15 depending on timing of previous pruning.
c. *Flower shape*.—Urceolate.
d. *Flower fragrance*.—Jasmine.
e. *Immature flower color*.—Pantone Reed Yellow 13-0915.
f. *Pollen staining*.—Good, 95% viable when stained with acetocarmine red.
g. *Self-compatibility*.—Poor, based on 2015 trial cross results: 8% of self-pollinated flowers reached maturity compared to 91% of flowers reached maturity when pollinated with pollen of 'Biloxi' (not patented).

Corolla:

a. *Color*.—Pantone Antique White 11-0105.
b. *Length*.—Average of 10.78 mm.
c. *Width*.—Average of 8.59 mm.
d. *Aperture width*.—Average of 4.31 mm.
e. *Anthocyanin coloration of corolla at time of anthesis*.—Low.
f. *Corolla ridges*.—Present, distinct.
g. *Protrusion of stigma*.—Average of −0.6 mm below lip of corolla (recessed).

Inflorescence:

a. *Length*.—Average of 46.3 mm.
b. *Diameter*.—Average of 33.73 mm.
c. *Length of peduncle*.—Average of 31.31 mm.
d. *Surface texture of peduncle*.—Smooth.
e. *Color of peduncle*.—Pantone Spinach Green 16-0439.
f. *Length of pedicel*.—Average of 10.98 mm.
g. *Surface texture of pedicel*.—Smooth.
h. *Color of pedicel*.—Pantone Green Oasis 15-0538.
i. *Number of flowers per cluster*.—Average of 6.4.
j. *Flower cluster density*.—Low.

Calyx (with sepals):

a. *Diameter*.—6.504 mm.
b. *Color* (*sepals*).—Pantone Lettuce Green 13-0324.
c. *Calyx surface*.—Smooth.

Stamen:

a. *Length*.—Average of 8.52 mm.
b. *Number per flower*.—10.
c. *Filament color*.—Pantone Celery Green 13-0532.

Pistil:

a. *Length*.—Average of 8.53 mm.
b. *Ovary color* (*exterior*).—Pantone Spinach green 16-0439.
c. *Style*.—Length — Average of 6.66 mm.

Anther:

*a. Length.*—Average of 3.8 mm.

*b. Number.*—10.

*c. Color.*—Pantone Burnt Orange 16-1448.

Pollen:

*a. Abundance.*—Medium.

*b. Color.*—Pantone Winter White 11-0507.

FRUIT

General:

*a. Time of fruit ripening.*—In Tala, Mexico harvest can begin in October, depending on timing of previous season's pruning.

*b. Time of 50% maturity.*—In Tala, Mexico December 5, depending on timing of previous season's pruning.

*c. Fruit development period.*—45 days.

*d. Mean harvest date.*—In Tala, Mexico peak harvest occurred on February 26, when plants were pruned the previous May.

*e. Mean date last pick.*—In Tala, Mexico the last harvest occurred on May 1, when plants were pruned the previous May.

*f. Cluster density.*—Medium.

*g. Berries per cluster.*—Average of 5.6 per cluster.

*h. Unripe fruit color.*—Pantone Lettuce Green 13-0324.

*i. Ripe berry color.*—Pantone Blue Fog 15-4008.

*j. Berry skin color after polishing.*—Pantone Shale 19-3903.

*k. Berry surface wax abundance.*—Good.

*l. Berry flesh color.*—Pantone White Jade 12-0315.

*m. Berry weight.*—Average of 2.2 g over the course of the harvest season, from 2 year old plants in Tala, Mexico.

*n. Berry height from calyx to scar.*—Average of 11.34 mm.

*o. Berry diameter.*—Average of 15.16 mm.

*p. Calyx aperture.*—Average of 5.20 mm.

*q. Calyx depth.*—Average of 1.6 mm.

*r. Pedicel length.*—Average of 7.43 mm.

*s. Pedicel surface texture.*—Smooth.

*t. Berry detachment force.*—Low.

*u. Berry shape.*—Oblong.

*v. Fruit stem scar.*—Small, dry.

*w. Berry flavor.*—Sweet, mildly aromatic.

*x. Sweetness when ripe.*—Good.

*y. Firmness when ripe.*—Very good. (1) Acidity when ripe — Low. (2) Storage quality — Excellent. (3) Suitability for mechanical harvesting — Low. (4) Self-fruitfulness — Poor. (5) Uses — Fruit production for the fresh market.

*z. Time of fruit ripening.*—In Tala, Mexico harvest can begin in October, depending on timing of previous season's pruning.

SEED

General:

*a. Seed abundance in fruit.*—Low.

*b. Seed color.*—Pantone Pecan Brown 17-1430.

*c. Seed dry weight.*—Approximately 3 mg.

*d. Seed length.*—Average of 2.00 mm.

COMPARISON BETWEEN PARENTAL AND COMMERCIAL CULTIVARS

TABLE 1

Comparison Table

| Denomination of similar variety | Characteristic for comparison | State of expression of similar variety | State of expression of candidate variety (FCM12-087) |
|---|---|---|---|
| FL00-180 (not patented | Fruit stem scar | Very small | Small |
| FL00-180 (not patented) | Leaf shape | Elliptic to lanceolate | Elliptic to ovate |
| FF-124 (pollen parent, unpatented) | Fruit firmness | Soft | Very firm |
| Biloxi (not patented) | Leaf margin | Slightly serrate | Entire |
| Ventura (U.S. Pat. No. PP24,606) | Length of internode | Long | Short |

The invention claimed is:

1. A new and distinct variety of blueberry plant named 'FCM12-087' substantially as illustrated and described herein.

* * * * *